United States Patent
Ren

(10) Patent No.: US 6,379,718 B2
(45) Date of Patent: Apr. 30, 2002

(54) USE OF PLANT EXTRACTS FOR TREATMENT OF ACNE AND FURUNCLE

(75) Inventor: Kaijun Ren, 1211 Spinnaker Way, Sugar Land, TX (US) 77478

(73) Assignee: Kaijun Ren, Sugar Land, TX (US)

(*) Notice: Subject to any disclaimer, the term of this patent is extended or adjusted under 35 U.S.C. 154(b) by 0 days.

(21) Appl. No.: 09/745,455

(22) Filed: Dec. 21, 2000

Related U.S. Application Data

(63) Continuation of application No. 09/350,342, filed on Jul. 14, 1999, now Pat. No. 6,183,747.

(51) Int. Cl.⁷ .................. A01N 65/00; A61K 35/78
(52) U.S. Cl. .................. 424/758; 424/725; 514/859
(58) Field of Search ............... 424/725, 758; 514/859

(56) References Cited

U.S. PATENT DOCUMENTS

| | | | |
|---|---|---|---|
| 4,795,739 A | * | 1/1989 | Lifson et al. |
| 4,985,248 A | * | 1/1991 | Liu |
| 5,484,889 A | * | 1/1996 | Lee-Huang et al. |
| 5,578,307 A | * | 11/1996 | Wunderlich et al. |
| 5,929,047 A | * | 7/1999 | Nakano |

FOREIGN PATENT DOCUMENTS

| | | | |
|---|---|---|---|
| CN | 1084714 | * | 4/1994 |
| CN | 1205202 | * | 1/1999 |
| JP | 54132227 | * | 10/1979 |
| JP | 04299938 | * | 10/1992 |
| JP | 06040882 | * | 2/1994 |
| WO | 97/04791 | * | 2/1997 |

OTHER PUBLICATIONS

Lee, C. J. Agric. Assoc. China. No. 127, pp. 68–76, abstract enclosed, 1984.*
Singh et al. Toxicol. Lett. vol. 94 (1), pp. 37–46, Jan. 1998.*

* cited by examiner

Primary Examiner—Christopher R. Tate
(74) Attorney, Agent, or Firm—Moser, Patterson & Sheridan, LLP

(57) ABSTRACT

Novel herbal extracts provide potent efficacy in the treatment of acne and furuncle. The formulated extracts of *Momordica charantia* L. are from either the whole plant or parts of the plant. The extracts have been formulated into aqueous solution, pads, and/or lotion. These formulations have been provided to treat acne and furuncle 2 to 3 times a day. It has demonstrated the ability to manage various grades of acne, from mild, moderate to severe, which include comedos, papules, pustules and nodules. Significant improvement is visible within five days. There are no observed either long-term or short-term side reactions.

12 Claims, No Drawings

USE OF PLANT EXTRACTS FOR TREATMENT OF ACNE AND FURUNCLE

This is a continuation of application(s) Ser. No. 09/350,342 filed on Jul. 14, 1999, now U.S. Pat. No. 6,183,747.

BACKGROUND OF INVENTION

Field of Invention

This invention relates to the use of the extract from the whole plant or a part of the plant as a novel potent agent for the treatments of acne and furuncle.

Background of the Invention

Acne vulgaris, also called acne, pimple, or break out, is the most common disease of the pilosebaceous unit of the skin. It generally appears in the second decade of life. It effects nearly 80 percent of persons at some time between the ages of 11 and 30 years. It is estimated that 30 percent of teenagers have acne of sufficient severity to required medical treatment. Acne is most commonly distributed on the face and to a lesser degree on the back and chest. It can persist for years and result in disfigurement and permanent scarring of the skin. 20% of adults are plagued with low-grade persistent acne. There is a huge market demand in the search for a potent anti-acne agent. In the last couple of decades in research, there is still a deficit in the potent efficacy and low toxicity of medicines to treat acne.

Acne is the result of the hypercornification of sebaceous follicles that are found over most of the body surface, but is the largest and most numerous on the face, chest, and upper back. In normal conditions, the cornified layer of the follicle remains thin. When the persistent cohesion between cells retards desquamation, it causes the thickening of the ductal epithelium to narrow the ductal lumen. The process of ductal hypercornification causes the formation of a micromedo that may evolve into either a comedo or an inflammatory lesion.

Androgen is one of most important factors to cause an increased production of sebum. From the age of puberty period and up, the adrenal glands mature and secrete an increased amount of androgen to increase the activity of sebaceous glands and produce more sebum. Males produce 10 times as much androgen as females, so it is not surprising that more males develop severe cases of acne.

A resident anaerobic organism, propionibacterium acnes, proliferates in the environment created by the mixture of the excessive sebum and follicular cells arid produces chemotatic factors and inflammatory mediators that may lead to inflammation.

Acne may also be exacerbated by several chemicals (drugs), such as iodides, bromides, glucocorticoids, and lithium, as well as the application of oil-containing compounds.

In occupational cases, acne prone workers placed in environments in which there is contact with oils frequently have pore occlusion problems. Hot humid environments may also cause sufficient hydration and swelling of the skin to predispose the skin to acne.

Furuncle is also a very common skin disease. It is the focal suppurative inflammation of hair follicles. Furuncle may occur in the hair follicles anywhere on the body, but they are most common on the face, neck, back, armpit, buttocks, and thighs. Almost everyone has had some experience with furuncles. The painful swelling of the skin is caused by a deep bacterial infection of the skin. It can occur singly or in multiples. Furuncle can be very painful if it occurs in the areas like the ear canal or the nose. Furuncles should be treated by a health care provider if it occurs by the nose. The condition that furuncles develop as they close and/or expand and join together is called carbunculosis.

With a couple dozen of acne medications out on the market, it is difficult for consumers to find a good product that really works for them because there are only a few that can actually treat acne. Most products contain basically the same ingredients: retinoide and its derivatives, benzyl peroxide, salicylic acid, sulfur, antibiotics, etc. Most are only effective for a short period of time and possess many side reactions.

Most of the over counter medications contain salicylic acid, sulfur, benzyl peroxide, amino acids, etc. Most can only treat a minor aspect of acne. These topical creams, lotions, ointments and cleansers can only attack the end results of acne, but not the causes. They can not prevent future outbreaks.

The prescribed topical cream and other formulations, like retin-A and its derivatives and antibiotics (benzamycin), may be able to treat a part of the acne problem, but the side reactions which they cause [to] make the benefits less than the problems. They strip off layers of skin, dry and irritate skin, and make skin more susceptible to sun burns.

The other current treatment is systemic treatment, such as antibiotics. It is about two thirds acne reacting under these treatments. This is a long term treatment. Other than their many side reactions, antibiotics also destroy the balance of the body's bacterial system, which will create additional problems.

Currently, the common treatment of furuncle includes warm, wet compresses of the furuncle several times a day. Antibiotic soaps, topical antibiotics (applied to a localized area of the skin) are of little benefit once the furuncle has formed. Systemic antibiotics may also help to control the infection.

Based on the factors of the acne medication market, side reactions are the most common problems encountered with the current acne medications. Some medications possess potent treatment, but the patients have to stop using the drug due to the adverse effects that make their skin worse than before.

SUMMARY OF THE INVENTION

The basic pathology of acne includes two major factors, inflammation (bacterial) and hypercornification of sebaceous follicles. A good therapeutic should at least have the ability to solve these two problems. The conventional methods of acne treatment, which may be classified into clinical, cosmetic and self treatment, have not provided total acne control and low side reactions and can be painful processes. Therefore, an objective of providing a relatively safe and effective medicine is still in demand.

The present invention relates to novel potent therapeutics for acne and furuncle. In the present invention, the composition has been demonstrated to manage the different grade of acne, from mild or moderate to severe. It includes the treatment of the symptoms of severe acne, such as comedo, pustules and nodules. It does not show any kind of side reactions.

Many herbs have a long history of being used in the treatment of bacteria, viruses and fungi. The fruit, bitter melon, of the plant, Momordica charantia L., has been used as a diet for a long period of time in different countries. It has also been used as an antibiotic, antioxidant, antidiabetic, and hypotensive agent and so on. In the present invention, the extracts of fruit, leaf, vine, and root have been investigated by HPLC and UV. They contain similar ingredients. The extract of the leaf indicates more components than others and has shown more potent efficacy in the control of acne and furuncle.

The practiced use of the extraction is formulated with the addition of organic and inorganic acids, such as a-hydroxy acid, fumaric acid, HCl and so on, to make the pH of the solution from 4–5. This process may add some benefits to the treatment:

1. Precipitate tannic acid and other components that may block the pilosebaceous layer of the skin.
2. Lower pH levels may soften the pilosebaceous tube to increase the elimination of sebum and keratinous debris.
3. Lighter color of the extract.
4. A lower pH environment to prevent growth of bacteria.

The preparations of the extract can be in different formulations: water solution, pads and lotion.

Therefore, the present invention is related to the novel discovery of an acne and furuncle treatment which is characterized by using extracts of *Momordica charantia* L., the extraction procedure, and the formulations.

One of the objectives of the present invention is to provide new uses of the herbal medicine that can treat acne and furuncle.

Another objective of the present invention is to provide a process for preparing the herbal medicine to treat acne and furuncle.

Another objective of the present invention is to provide better and convenient formulations to treat acne and furuncle.

Further and other objectives of the present invention may be illustrated from the following description of the present invention in detail.

DETAILED DESCRIPTION OF THE INVENTION

According to the present invention, a process of preparing herbal medicine comprises treating fresh material, dried raw material, different parts of the plant, and different formulations. The typical processes are listed in the following pages.

200 g fresh plant was collected and washed. The washed plant was left so the surface water could dry. It was then grinded to an almost pulp-like texture and squeezed through a gauze to obtain as much liquid as possible. All of the liquid was collected and then centrifuged at high speed, which was not less than 3500 rpm. The upper clean liquid was collected. The solution was about 120 ml and its pH was between 6 to 6.5.

The formulation of the extracts was performed with organic and inorganic acids. The typical sample used was glycolic acid. The acid was dissolved in water and the pH was adjusted to about pH 3.8 with saturated sodium hydroxide solution. The final concentration of glycolic acid was 50%. Under room temperature and stirring, the glycolic acid solution was added drop by drop to the centrifuged clean solution until the final concentration of glycolic acid in the extract was 5% or the pH of the extraction was above 4. There was a lot of precipitate and the formulated solution was allowed to stand overnight. The formulated solution was centrifuged to remove the precipitate. The concentration of the solution can be increased by lyophilization or evaporation under vacuum.

Dried raw materials are easier to store and solve the seasonal problem of obtaining natural products. 100 g of the fresh plant was dried naturally to form 15.3 g dry powder of the plant. 100 g of fresh root resulted in 12.1 g of dry root.

In a 450 ml beaker, 160 ml of water were added to 20 g of the dry powder raw material. The mixture was boiled for 20 minutes. The solution was filtrated and the residue was squeezed to near dry while the mixture still was warm. The combination of the solutions was about 110 ml. If the volume was greater than 110 ml, part of the water was evaporated to reach that volume. This volume is similar to that of the fresh material. The pH of the solution was around 8. The HPLC and UV results were almost identical between the fresh and dry materials. The HPLC conditions are as follows:

Column: C18, 300 Å, 5$\mu$, 4.6 mm×2500 mm
Solvent A: 100% water
Solvent B: 5% water in acetonitrile
Gradient: 0–30% of B in 30 min.
Flow rate: 1 ml per min.
Detector: UV 214 nm The formulated extract from the dried plant was treated by the same procedure as in the fresh material. The amount of acidity did not have a significant difference. The HPLC and UV demonstrated the similarity in both.

The extracts have a natural herb smell. It is uncomfortable for some people. To remove the smell, 3 g of active carbon were added to 100 ml of the formulated solution and stirred at room temperature for 5 min. The active carbon was filtrated to obtain a clean solution. This solution did not have the strong smell but a slightly comfortable, sweet smell. The UV spectra showed that the absorbency after 460 nm had disappeared. If the de-smell time had lasted to 1 hour, the solution had de-colored and had turned to a light yellow tone. The UV spectra showed that the absorbency after 340 nm had disappeared.

In the present invention, the best part or the whole plant is necessary to serve the treatments that had been investigated. Each part of the plant, leaf, melon, root, and vine, had been studied by HPLC and UV spectra. All of them were fresh parts of the plant and were grinded. The liquid was squeezed out from the grinded material through gauze. The liquids were centrifuged and the upper solutions served as the samples for HPLC and UV spectra. By the results of HPLC, leaf, root and melon most likely contained the same components. Based on the strength of absorbency, the vine extraction contained less of the components than that of the before mentioned three. In the results of UV spectra, the melon had no strong absorbency after 340 nm. The root had no strong absorbency after 380 nm. The vine had no strong absorbency after 426 nm. The leaf had the highest absorbency in the group. It had no strong absorbency after 470 nm. Therefore, all of the plant could be used as raw material for the treatment of acne and furuncle. The order of the best parts for the treatments is: leaf, root, melon, and vine.

In the present invention, the different formulations have also been described. The acidified solution could be directly used for acne and furuncle treatment. The concentration can be increased for different levels of the diseases. Generally speaking, the more severe the form of acne and furuncle, the higher the concentration used. The normal concentration levels range from 1 to 2 times the original concentration.

For convenience, pads had been made by addition of the solution to 2⅛ inch cotton pads. This formulation was much more convenient for people to use, specifically for young adults. To confirm that the pads release a solution which contains the same quality and quantity of material as the original aqueous solution, the solution in the pads was squeezed out and compared with original aqueous solution by HPLC and UV spectra. Both results indicated that the both solutions contained exactly the same components in both quality and quantity.

In the present invention, the other formulation of the extract was a lotion preparation. The formulated extract could be added to normal skin care cream or lotion. To maintain the same concentration of the solution in the lotion, the extract needed to be concentrated. It can be performed under a normal boiling evaporation procedure. To avoid possible overheating, which may destroy some components, the best procedures are either lyophilization or evaporation under vacuum. The final volume of the solution depends on the concentration of the lotion. The final solution should be a clean solution with no precipitate. This is important in making a homogenous lotion and achieving the expected treatment.

THE TREATMENT AND RESULTS

For a normal acne and furuncle case (mild or moderate level), the skin treatment composition described herein may be used twice a day, in the morning and in the evening. A thin layer is applied on the problem areas after the face is washed and dried. For more severe cases, one may increase the application times. Significant improvement will occur in 3–5 days after the treatment. Some results are summarized in the following tables.

TABLE 1

The Treatment of Acne

| Number Involved | Age (Year) | History (Year) | Number in Each Level Comedo Papulopustule Nodule | | | Efficacy (%) | Comparison with Others Medications |
|---|---|---|---|---|---|---|---|
| 6 | 17–36 | 4–20 | 6 | 6 | 1 | 100 | Best |

TABLE 2

The Treatment of Furuncle

| Number Involved | Age (year) | History (day) | Treatment (day) | Size of Furuncle (cm) | Results |
|---|---|---|---|---|---|
| 5 | 16–47 | 2–100 | <3 | 0.5–1.5 | Disappear |

What is claimed is:

1. A process for producing a skin treatment composition for treating acne and furuncle containing an extract of *Momordica charactia* L., comprising:

grinding one or more parts of *Momordica charactia* L. plant to a pulp-like texture;

pressing liquid from the ground plant;

centrifuging the pressed liquid;

collecting upper clean centrifuged liquid; and formulating a solution by adding an effective amount of an acid to the clean centrifuged liquid to produce a skin treatment composition.

2. The process of claim 1, further comprising:

centrifuging the solution; and removing precipitate from the centrifuged solution.

3. The process of claim 2, further comprising:

filtrating the centrifuged solution through active carbon.

4. The process of claim 3, further comprising:

soaking one or more pads in the filtrated solution.

5. The process of claim 2, further comprising:

increasing the concentration of the centrifuged solution by lyphilization or evaporation under vacuum.

6. The process of claim 5, further comprising:

adding the concentrated solution to a skin care cream or lotion.

7. A process for producing a skin treatment composition for treating acne and furuncle containing an extract of *Momordica charactia* L., comprising:

boiling dried powder from one or more parts of *Momordica charactia* L. plant in water;

filtrating residue from the boiled mixture; and formulating a solution by adding an effective amount of an acid to the filtrated mixture to produce a skin treatment composition.

8. The process of claim 7, further comprising:

centrifuging the solution; and removing precipitate from the centrifuged solution.

9. The process of claim 8, further comprising:

filtrating the centrifuged solution through active carbon.

10. The process of claim 9, further comprising:

soaking one or more pads in the filtrated solution.

11. The process of claim 8, further comprising:

increasing the concentration of the centrifuged solution by lyophilization or evaporation under vacuum.

12. The process of claim 11, further comprising:

adding the concentrated solution to a skin care cream or lotion.

* * * * *